US005914391A

United States Patent [19]

Gerber et al.

[11] Patent Number: 5,914,391

[45] Date of Patent: Jun. 22, 1999

[54] STABILIZED COMPOSITIONS CONTAINING HEMOGLOBIN

[75] Inventors: Michael J. Gerber, Denver; Douglas L. Looker; Bruce A. Kerwin, both of Lafayette, all of Colo.

[73] Assignee: Baxter Biotech Technology Sárl, Neuchatel, Switzerland

[21] Appl. No.: 08/913,036

[22] PCT Filed: Aug. 10, 1995

[86] PCT No.: PCT/US95/10232

§ 371 Date: Nov. 17, 1997

§ 102(e) Date: Nov. 17, 1997

[87] PCT Pub. No.: WO96/27388

PCT Pub. Date: Sep. 12, 1996

Related U.S. Application Data

[63] Continuation-in-part of application No. 08/417,644, Apr. 5, 1995, and a continuation-in-part of application No. 08/399, 899, Mar. 7, 1995, abandoned.

[51] Int. Cl.$^{6}$ .......................... A61K 35/14; A61K 38/06

[52] U.S. Cl. ................................................ 530/385; 514/6

[58] Field of Search ................................ 530/385; 514/6

[56] References Cited

U.S. PATENT DOCUMENTS

| | | | |
|---|---|---|---|
| 4,506,018 | 3/1985 | North, Jr. | 436/10 |
| 5,028,588 | 7/1991 | Hoffman et al. | 514/6 |
| 5,194,590 | 3/1993 | Sehgal et al. | 530/385 |
| 5,733,873 | 3/1998 | Osterberg et al. | 514/12 |

FOREIGN PATENT DOCUMENTS

| | | |
|---|---|---|
| 0115077 | 8/1984 | European Pat. Off. . |
| 0142125 | 5/1985 | European Pat. Off. . |
| 9109615 | 7/1991 | WIPO . |
| 9202239 | 2/1992 | WIPO . |
| 9203153 | 3/1992 | WIPO . |
| 9401452 | 1/1994 | WIPO . |
| 9514038 | 5/1995 | WIPO . |
| WO 9634889 | 7/1996 | WIPO . |

OTHER PUBLICATIONS

Adachi et al./Comparison of Mechanism of Hemoglobin Denaturation by Heat and Mechanical Shaking/Fed. Proc./(1976) 35: 1392 #180.

Pristoupil & Marík/on the Hydronamic Instability of Hemoglobin Solutions/Biomat. Art. Cells, Art. Org./(1990) 18(2): 183–188.

Moore et al./Evalution of Methemoglobin Formation During the Storage of Various Hemoglobin Solutions/Artif Organs.(1992) 16(5): 513–518.

Feola et al./Mechanisms of Toxicity of Hemoglobin Solutions/Biomat., Art. Cells, Art. Org., (1988) 16(1–3): 217–226.

Adachi & Asakura/Aggregation and Crystallization of Hemoglobins A,S, and C—Probable Formation of Different Nuclei for Gelation and Crystallization/JBC/(1981) 256(4): 1824–1830.

Adachi & Asakura/Effect of 2,3–Diphosphoglycerate and Inositol Hexaphosphate on the Stability of Normal and Sickle Hemoglobins/Biochemistry/(1974) 13(24): 4976–4982.

*Primary Examiner*—Robert J. Hill, Jr.

*Assistant Examiner*—Abdel A. Mohamed

*Attorney, Agent, or Firm*—Senniger, Powers, Leavitt & Roedel

[57] ABSTRACT

The present invention relates to hemoglobin compositions stabilized against the formation of aggregates. Such compositions contain at least a surfactant, said surfactant not being an adduct of a polymer and an anionic ligand. The present invention further relates to methods of making such hemoglobin compositions.

33 Claims, 2 Drawing Sheets

Filter Pressure (mm Hg)
120
100
80
60
40
20
0
0
10
20
30
40
50
Time (min)

STABILIZED COMPOSITIONS CONTAINING HEMOGLOBIN

This is a 371 of PCT/US95/10232, filed Aug. 10, 1995 which is a CIP of application Ser. No. 08/417,644, filed Apr. 5, 1995 and a CIP of application Ser. No. 08/399,899, filed Mar. 7, 1995, now abandoned.

FIELD OF INVENTION

The present invention relates to novel hemoglobin-containing compositions stabilized to inhibit aggregate formation therein.

BACKGROUND OF THE INVENTION

The oxygen carrying portion of red blood cells is the protein hemoglobin. Hemoglobin is a tetrameric protein molecule composed of two identical alpha globin subunits ($\alpha_1$, $\alpha_2$), two identical beta globin subunits ($\beta_1$, $\beta_2$) and four heme molecules. A heme molecule is incorporated into each of the alpha and beta globins to give alpha and beta subunits. Heme is a large macrocyclic organic molecule containing an iron atom; each heme can combine reversibly with one ligand molecule such as oxygen. In a hemoglobin tetramer, each alpha subunit is associated with a beta subunit to form two stable alpha/beta dimers, which in turn associate to form the tetramer. The subunits are noncovalently associated through Van der Waals forces, hydrogen bonds and salt bridges.

Hemoglobin in solution can be used, for example, as a blood substitute, as a therapeutic for enhancing hematopoiesis, as a means of delivering oxygen or enhancing oxygen delivery to tissues, for hemoaugmentation, for the binding or delivery of nitric oxide or other non-oxygen ligands, as a drug delivery vehicle, as a cell culture additive, as a reference standard, and as an imaging agent. However, storage of hemoglobin solutions can be problematic. Proteins in solution can form aggregates upon long term storage, changes in temperature during storage, or mechanical agitation (Cleland, et al., *Crit. Rev. Ther. Drug Carrier Systems* 10: 307–377 (1993). To address these problems, many unique formulations have been developed for the stabilization of different proteins in solution. For example, both naturally derived and recombinantly produced proteins have been formulated in solutions containing disaccharides and amino acids (factor VII or factor IX solutions described in PCT Publication WO 91/10439 to Octapharma), human serum albumin (interleukin-2 solutions described in U.S. Pat. No. 4,645,830 to Yasushi et al.), and glycine, mannitol and non-ionic surfactants (human growth hormone solutions described in U.S. Pat. No. 5,096,885 to Pearlman et al.). Although some general guidance is available for the determination of suitable components for formulations for protein solutions, because of the unique nature of individual proteins, no single formulation is suitable for all different proteins. Indeed, Cleland et al. (1993) state that the creation of a formulation that minimizes protein degradation is difficult because there are many factors that interact to determine protein degradation in a formulation. They go on to state that "protein degradation . . . cannot be predicted a priori and must be determined for each protein".

To extend the storage stability of hemoglobin solutions by limiting autooxidation, hemoglobin has been formulated with reducing agents such as cysteine or dithionite, mannitol, glucose and/or alpha tocopherol (Shorr et al., PCT Publication WO 94/01452), in saline solutions or lactated Ringer's solutions that have been modified by the addition of, for example ascorbate, ATP, glutathione and adenosine (Feola et al., PCT Publication WO 91/09615; Nelson et al, PCT Publication WO 92/03153), under deoxygenated conditions with no exogenous reductants (Kandler and Spicussa, PCT Publication WO 92/02239), or in the presence of reducing enzyme systems (Sehgal et al., U.S. Pat. No. 5,194,590). These hemoglobin formulations have been designed to minimize autooxidation of the protein molecule, but none have been designed that specifically reduce the aggregation of the hemoglobin molecules during storage.

Nonetheless, the aggregation of hemoglobin molecules during storage poses significant problems. Moore et al., *Art. Org.* 16: 513–518 (1992) caution that hemoglobin should not be stored in the frozen state due to the formation of aggregates or precipitates. Moreover, the formation of aggregates in hemoglobin solutions agitated at room temperature has been observed in numerous formulations (Pristoupil and Marik, *Biomat. Art. Cells. Art. Org.,* 18: 183–188, 1990; Adachi and Asakura, *J. Biol. Chem.,* 256: 1824–1830, 1981; Adachi and Asakura, *Biochem. 13: 4976–4982,1974*). This aggregation of the hemoglobin protein molecule typically does not occur as a result of autooxidation of the hemoglobin heme iron, but rather by interaction of the hemoglobin molecules (Adachi et al., *Fed. Proc.* 35: 1392 (1976). Aggregates in hemoglobin solutions can increase immunogenicity, reduce functionality and reduce the activity of the protein solution (Cleland et al., supra; Feola et al., *Biomat. Art. Cells Art. Org.* 16: 217–226 (1988).

Accordingly, there is a need for hemoglobin compositions stabilized against the formation of aggregates. The present invention satisfies this need and provides related advantages as well.

SUMMARY OF THE INVENTION

The present invention relates to compositions containing hemoglobin wherein the hemoglobin is stabilized with a surfactant to inhibit the formation of aggregates. In one embodiment, compositions of the invention contain about 0.001% to about 90% by weight to volume hemoglobin and 0.01 to 1% (weight to volume) of a surfactant and can also include 0–200 mM of one or more buffers, 0–200 mM of one or more alcohols or polyalcohols, 0–300 mM of one or more salts, 0–100 μM of one or more chelating agents and 0–5 mM of one or more reducing agents. In a further embodiment, the compositions can contain 0.01–50% by weight to volume of hemoglobin, 0–50 mM of one or more buffers, 0–200 mM of one or more salts, 0.02%–0.5% (weight to volume) of one or more surfactants, 0–5 mM of one or more reducing agents, 5–50 μM of one or more chelating agents, and is at a pH of about 6.8 to 7.8. Another aspect of the invention are compositions containing about 1 to about 20% by weight to volume of hemoglobin, 5–15 mM sodium phosphate, 100–185 mM sodium chloride, 0.02%–0.08% (weight to volume) polysorbate 80,1–4 mM of ascorbate, 2–40 μM ethylene diamine tetraacetic acid, and is at pH of about 6.8 to 7.6. A still further embodiment of the present invention is a method for stabilizing compositions containing hemoglobin to inhibit the formation of aggregates comprising adding to the composition a stabilizing amount of a surfactant.

Other features and advantages of the invention will be apparent from the following description of the invention and from the claims.

Open circles show the filter pressure for the mannitol/bicarbonate formulation that did not contain polysorbate 80. Filled circles show the filter pressure for the mannitol/bicarbonate formulation that contained 0.03% polysorbate 80.

Figure 2:
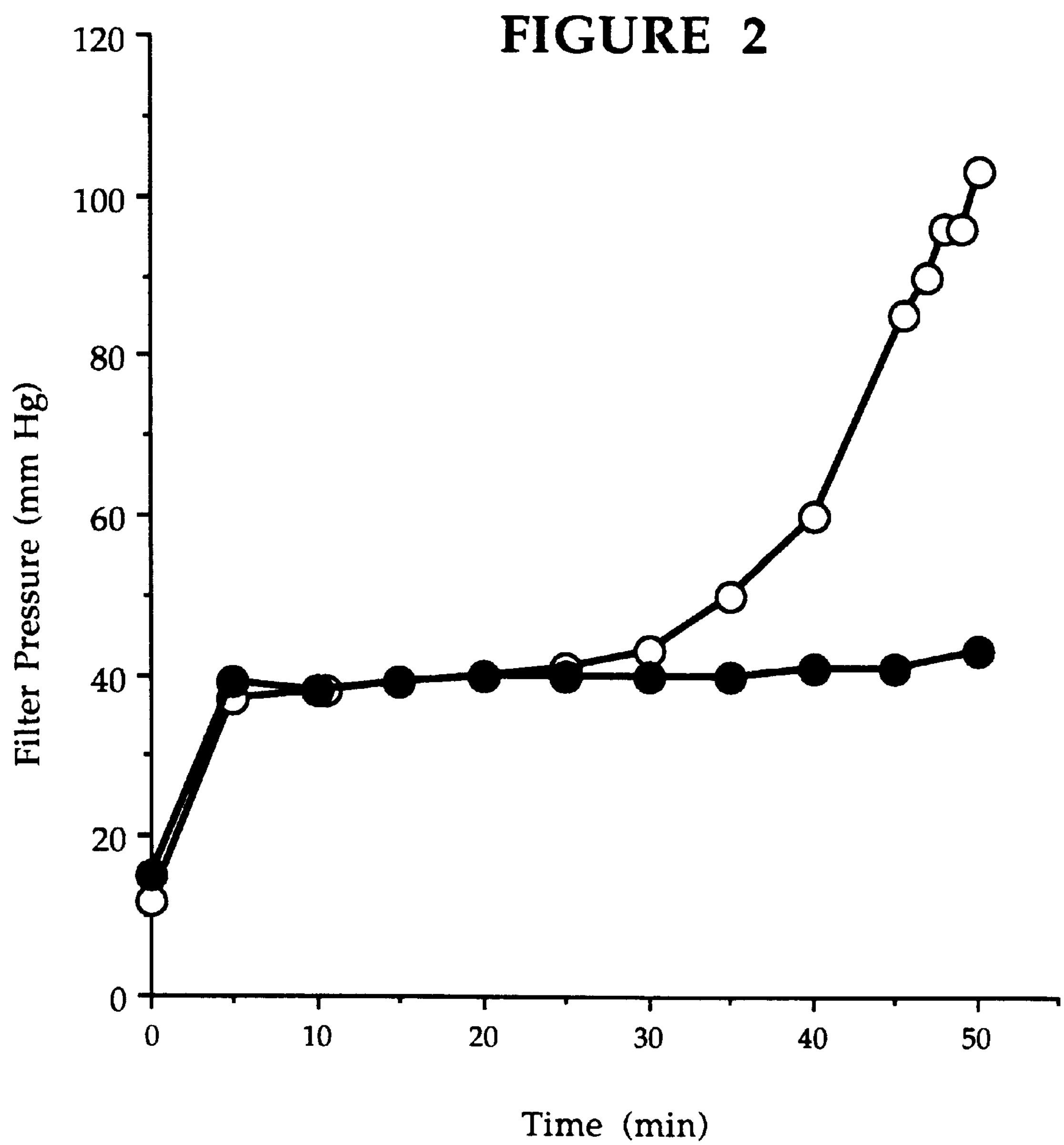

FIG. 2 shows filter pressure during filtration of hemoglobin formulated in a sodium chloride/sodium phosphate buffer system. Open circles show the filter pressure for the sodium chloride/sodium phosphate formulation that did not contain polysorbate 80. Filled circles show the filter pressure for the sodium chloride/sodium phosphate formulation that contained 0.03% polysorbate 80.

DETAILED DESCRIPTION OF THE INVENTION

Hemoglobin is generally a tetramer composed of two alpha globin subunits ($\alpha_1$, $\alpha_2$) and two beta globin subunits ($\beta_1$, $\beta_2$). There is no sequence difference between $\alpha_1$ and $\alpha_2$ or between $\beta_1$ and $\beta_2$. The subunits are noncovalently associated by Van der Waals forces, hydrogen bonds and salt bridges.

Hemoglobin is readily available from a number of natural and recombinant sources. For example, slaughter houses produce very large quantities of hemoglobin-containing blood. Particular species or breeds of animals which produce a hemoglobin especially suitable for a particular use can be specifically bred in order to supply hemoglobin. Transgenic animals can be produced that can express non-endogenous hemoglobin (Logan, J. S. et al., PCT Application Number PCT/US92/05000). Human hemoglobin can be collected from outdated human blood that must be discarded after a certain expiration date.

In addition to extraction from animal sources, the genes encoding subunits of a desired naturally occurring or mutant hemoglobin can be cloned, placed in a suitable expression vector and inserted into an organism, such as a microorganism, animal or plant, or into cultured animal or plant cells or tissues. These organisms can be produced using standard recombinant DNA techniques and hemoglobin produced by these organisms can then be expressed and collected (as described, for example, in Hoffman, S. J and Nagai, K. in U.S. Pat. No. 5,028,588 and Hoffman, et al., WO 90/13645, both herein incorporated by reference).

Purification of hemoglobin from any source can be accomplished using purification techniques which are known in the art. For example, hemoglobin can be isolated and purified from outdated human red blood cells by hemolysis of erythrocytes followed by chromatography (Bonhard, K., et al., U.S. Pat. No. 4,439,357; Tayot, J. L. et al., EP Publication 0 132 178; Hsia, J. C., EP Patent 0 231 236 B1), filtration (Rabiner, S. F. (1967) et al., *J. Exp. Med.* 126: 1127–1142; Kothe, N. and Eichentopf, B. U.S. Pat. No. 4,562,715), heating (Estep, T. N., PCT publication PCT/US89/014890, Estep, T. N., U.S. Pat. No. 4,861,867), precipitation (Simmonds, R. S and Owen, W. P., U.S. Pat. No. 4,401,652; Tye, R. W., U.S. Pat. No. 4,473,494) or combinations of these techniques (Rausch, C. W. and Feola, M., EP 0 277 289 B1). Recombinant hemoglobins produced in transgenic animals have been purified by chromatofocusing (Townes, T. M. and McCune, PCT publication PCT/US/09624); those produced in yeast and bacteria have been purified by ion exchange chromatography (Hoffman, S. J and Nagai, K. in U.S. Pat. No. 5,028,588 and Hoffman, et al., WO 90/13645).

As used herein, "hemoglobin" means a hemoglobin molecule comprised of at least two globin subunits or domains (dimeric). Hemoglobin can be free in solution or contained within in a cell, liposome or the like. Any globin subunit, whether of natural or recombinant origin, of any hemoglobin, can be crosslinked or genetically fused to another globin subunit. Such crosslinking or genetic fusion can occur within a single hemoglobin molecule or between two or more hemoglobin molecules. Particularly preferred hemoglobins are tetrameric hemoglobins, whether or not genetically fused or chemically crosslinked, and multiples of tetrameric hemoglobins (e.g. octamers, dodecamers, etc.), however produced. Therefore, the term hemoglobin encompasses any for example, non-crosslinked hemoglobin, chemically crosslinked hemoglobin, or genetically fused hemoglobin. In addition, the hemoglobin can be either liganded with any ligand, such as oxygen, carbon monoxide or nitric oxide, or can be in the unliganded (deoxygenated) state.

"Surfactant" as used herein is intended to encompass any detergent that has a hydrophilic region and a hydrophobic region, and, for the purposes of this invention includes non-ionic, cationic, anionic and zwitterionic detergents. Suitable surfactants include, for example, N-laurylsarcosine, cetylpyridinium bromide, polyoxyethylene sorbitan monolaurate (also known as polysorbate 20 or "TWEEN" 20), polyoxyethylene glycol hexadecyl ether ("BRIJ" 35), or polyoxyethylene sorbitan monooleate (also known as polysorbate 80 or "TWEEN" 80). A non-ionic surfactant is preferable for the formulations described herein. Such non-ionic surfactants can be chosen from block co-polymers such as a polyoxamer or polyoxyethylene sorbitan fatty acid esters, for example, polysorbate 20 or polysorbate 80. Polysorbate 80 is preferred for the compositions of this invention.

A stabilizing amount of surfactant is an amount sufficient to inhibit the formation of aggregates in hemoglobin-containing compositions. Such aggregate formation can occur during, for example, long term storage, freezing and thawing, or mechanical agitation. Inhibition of such aggregate formation occurs when the aggregate formation in a composition containing hemoglobin and a surfactant is significantly inhibited relative to aggregate formation in the same composition containing hemoglobin that does not contain the surfactant. Significant inhibition of aggregation occurs when aggregate formation is at least 10% less in the hemoglobin containing composition with surfactant than in a comparable formulation that does not contain surfactant, preferably at least 50% less, more preferably at least 70% less, and most preferably at least 90% less.

"Aggregates" refers to hemoglobin molecules that can be soluble or insoluble and are detectable by aggregate detection methods such as visual inspection, light scattering methods such as spectrophotometry and dynamic light scattering, particle counting methods, filtration backpressure increases or other suitable methods for the determination of aggregates.

The compositions of the invention can be incorporated in conventional formulations including but not limited to tablets, capsules, caplets, compositions for subcutaneous, intravenous, or intramuscular injection or oral administration, reagent solutions for standardization of clinical instrumentation, large volume parenteral solutions useful as blood substitutes, etc. The compositions can be formulated by any method known in the art, including, for example, simple mixing, sequential addition, emulsification, and the like. The formulations of the invention comprise hemoglobin and surfactants as the active ingredients and can include other active or inert agents. For example, a parenteral therapeutic composition can comprise a sterile isotonic saline solution containing between 0.001% and 90% (w/v) hemoglobin. Suitable compositions can also include 0–200 M of one or more buffers (for example, acetate, phosphate, citrate, bicarbonate, or Good's buffers). Salts such as sodium chloride, potassium chloride, sodium acetate, calcium chloride, magnesium chloride can also be included in the compositions of the invention at concentrations of 0–2 M. In addition, the compositions of the invention can include 0–2 M of one or more carbohydrates (for example, reducing carbohydrates such as glucose, maltose, lactose or non-reducing carbohydrates such as sucrose, trehalose, raffinose, mannitol, isosucrose or stachyose) and 0–2 M of one or more alcohols or poly alcohols (such as polyethylene glycols, propylene glycols, dextrans, or polyols). The compositions of the invention also contain 0.005–1% of one or more surfactants. The compositions of the invention can also be at about pH 6.5–9.5. In another embodiment, the composition contains 0–300 mM of one or more salts, for example chloride salts, 0–100 mM of one or more non-reducing sugars, 0–100 mM of one or more buffers, and 0.01–0.5% of one or more surfactants. In a still further embodiment, the composition contains 0–150 mM NaCl, 0–10 mM sodium phosphate, and 0.01–0.1% surfactant, pH 6.6–7.8. Most preferably, the hemoglobin-containing composition includes 5 mM sodium phosphate, 150 mM NaCl, and 0.025% to 0.08% polysorbate 80, pH 6.8–7.6.

Other components can be added if desired. For example 0–5 mM reducing agents such as dithionite, ferrous salts, sodium borohydride, and ascorbate can be added to the composition, most preferably 0.5–3 mM ascorbate is added to the composition. Additional additives to the formulation can include anti-oxidants (e.g. ascorbate or salts thereof, alpha tocopherol), anti-bacterial agents, chelating agents such as, for example, ethylene diamine tetraacetic acid (EDTA) or ethylene glycol-bis(β-aminoethyl ether)N,N,N',N',-tetraacetic acid (EGTA), oncotic pressure agents (e.g. albumin or polyethylene glycols) and other formulation acceptable salts, sugars and excipients known to those of skill in the art.

Each formulation according to the present invention can additionally comprise inert constituents including carriers, diluents, fillers, salts, and other materials well-known in the art, the selection of which depends upon the particular purpose to be achieved and the properties of such additives which can be readily determined by one skilled in the art.

The formulation of the instant invention can be used to treat anemia, both by providing additional oxygen carrying capacity in a patient that is suffering from anemia, and by stimulating hematopoiesis. In addition, because the distribution of the hemoglobin in the vasculature is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation and the like.

The formulated hemoglobin solutions of the instant invention can also be used as replacement for blood that is removed during surgical procedures where the patient's blood is removed and saved for reinfusion at the end of surgery or during recovery (acute normovolemic hemodilution or hemoaugmentation).

Because the purified hemoglobin solutions of the instant invention can bind nitric oxide and other non-oxygen ligands as well as oxygen, the formulations of the instant invention are also useful for the binding or delivery of nitric oxide or non-oxygen ligands. These non-oxygen ligands can be bound or delivered both in vivo or in vitro. For example, the purified hemoglobin solutions of the instant invention may be used to remove excess nitric oxide from a living system. Excess nitric oxide has been implicated in conditions ranging from hypotension to septic shock. Likewise, nitric oxide or other non-oxygen ligands may be delivered to a system to alleviate a disease condition. For example, nitric oxide could be delivered to the vasculature to treat hypertension. Other therapeutic uses of the instant invention can include drug delivery and in vivo imaging.

The hemoglobin formulations of the present invention can also be used for a number of in vitro applications. For example, the delivery of oxygen by the purified hemoglobin solutions of the instant invention can be used for the enhancement of cell growth in cell culture by maintaining oxygen levels in vitro. Moreover, the purified hemoglobin solutions of the instant invention can be used to remove oxygen from solutions requiring the removal of oxygen, and as reference standards for analytical assays and instrumentation.

EXAMPLES

The following examples are provided by way of describing specific embodiments of the present invention without intending to limit the scope of the invention in any way.

EXAMPLE 1

Measurements of Aggregate Formation

Measurement of particles≧2 μm—Light obscuration functions by measuring the decrease in signal strength caused by a particle passing through a laser. By comparing the decrease in signal strength to that of a series of latex spheres of known size, the sizes of the particles in the sample were determined. Particles≧2 μm were measured by light obscuration with a HIAC/Royco (Silver Springs, Md.) particle counter model 8000A equipped with a model 3000 sampler. Measurements were made following dilution of the sample (0.5–1 ml aliquots) to 10 ml in 150 mM NaCl, 5 mM sodium phosphate buffer, pH 7.4. Numbers represent the cumulative particle counts≧2 μm.

Filter pressure assay—As a solution is passed through a filter, the filter is slowly blocked and the filter pressure increases as a function of aggregate accumulation on the filter. This method provides an indirect measurement of aggregation≧0.2 μm which is not detectable by the light obscuration described above. The ability of a hemoglobin-containing sample to block a 0.2 μm filter was determined using an "IVAC" infusion pump (San Diego, Calif.). Briefly, following shaking or freeze/thawing each sample was transferred to a 500 ml polyvinyl chloride bag and pumped at 500 ml/hr through a 0.2 μm "PALL" in-line filter (East Hills, N.Y.). The back pressure on the filter was monitored directly from the "IVAC" pump.

EXAMPLE 2

Determination of Concentration of Polysorbate 80 required to inhibit formation of aggregates≧2 μm during freeze/thaw Hemoglobin was expressed, prepared and purified as described in co-owned PCT publication number, WO 95/13034, filed Nov. 14,1994, entitled "Purification of Hemoglobin". Suitable concentrations of polysorbate 80 for reduction of aggregation were determined by subjecting hemoglobin formulated with increasing concentrations of polysorbate 80 to repeated freeze/thaw cycles. Aliquots (1.5 ml) of 50 mg/ml hemoglobin in 150 mM NaCl, 5 mM phosphate, pH 7.4, were formulated with and without polysorbate 80 and sealed in 3.5 ml glass vials. The samples were frozen at either −80° C. or −20° C. for 24 hour periods. On selected days two vials were removed from each freezer, slowly thawed in water at 25° C. and the number of aggregates determined using the HIAC/Royco Particle Counter. The remaining samples were thawed at room temperature then refrozen at either −80° C. or −20° C.

In the absence of polysorbate 80 the number of aggregates≧2 μm increased by approximately 3-fold at −20° C. (Table 1) and approximately 5-fold at −80° C. (Table 2) after five freeze/thaw cycles. The presence of 0.005–0.01% polysorbate 80 could not prevent the increase at either temperature and at −20° C. appeared to exacerbate the increase in aggregation seen in the absence of polysorbate. In contrast, 0.025–0.1% polysorbate 80 inhibited the formation of aggregates after the freeze/thaw cycles relative to the formation of aggregates in compositions that did not contain polysorbate by between approximately 28–46%. During the course of the freeze/thaws the number of aggregates in the samples containing 0.025% polysorbate 80 varied from 1–1.6-fold at −20° C. and from 1.2–1.9-fold at −80° C. Furthermore, the final degree of aggregation in formulations containing 0.05 to 0.1% polysorbate 80 was significantly less (~45–70%) than the aggregation observed in compositions that did not contain surfactant. The samples containing 0.025% polysorbate 80 or greater demonstrated a decreased tendency to aggregate compared to the samples containing 0.01% or less (inhibition of aggregate formation in the presence of 0.025% polysorbate was at least 25% relative to formulations that did not contain surfactant).

TABLE 1

Effect of Polysorbate 80 on particle aggregation: Freeze/Thaw −20° C.

| % (w/v) | Number Freeze/Thaw Cycles | | |
|---|---|---|---|
| Polysorbate 80 | 0 | 2 | 5 |
| 0.0% | 1500 | 3300 | 4200 |
| 0.005% | 3800 | 5100 | 7200 |
| 0.01% | 3000 | 4200 | 7500 |
| 0.025% | 2000 | 3200 | 3000 |
| 0.05% | 1400 | 1900 | 2300 |
| 0.1% | 970 | 1800 | 2200 |

TABLE 2

Effect of Polysorbate 80 on particle aggregation: Freeze/Thaw −80° C.

| % (w/v) | Number Freeze/Thaw Cycles | | |
|---|---|---|---|
| Polysorbate 80 | 0 | 2 | 5 |
| 0.0% | 1500 | 3300 | 7800 |
| 0.005% | 3800 | 5500 | 9000 |
| 0.01% | 3000 | 4300 | 5600 |
| 0.025% | 1955 | 3100 | 3600 |
| 0.05% | 1400 | 2700 | 2300 |
| 0.1% | 1000 | 2000 | 2400 |

EXAMPLE 3

Determination of Concentration of Polysorbate 80 required to inhibit formation of aggregates≧2 μm during mechanical agitation Hemoglobin was prepared as described in Example 2. Suitable concentrations of polysorbate 80 for reduction of aggregation were determined by subjecting hemoglobin formulated with increasing concentrations of polysorbate 80 to mechanical agitation. Aliquots (1.5 ml) of 50 mg/ml hemoglobin in 150 mM NaCl, 5 mM phosphate, pH 7.4, were formulated with and without polysorbate 80 and were sealed in 3.5 ml glass vials. The samples were then placed on their sides on an orbital shaker and shaken for 1 hour at 4° C. at 90, 120, 180 and 240 rpm. A 1 ml aliquot was removed and aggregates≧2 μm were counted using a HIAC/Royco Particle counter as described in Example 1. Because no aggregate formation occurred during the course of the experiment at 90 or 120 rpm, only the control data (no mechanical agitation, listed as 0 rpm in Table 3) and the data for 180 and 240 rpm are reported below (Table 3). Addition of the surfactant at a concentration of 0.025% or greater inhibited the formation of aggregates while addition of 0.01% of the surfactant did not demonstrate any significant protection against aggregation. At 240 rpm the sample containing 0.025% polysorbate 80 showed an increase in the number of aggregates compared to the 0.05% polysorbate 80 sample. In other experiments no increase in aggregation was observed by decreasing the polysorbate concentration from 0.05% to 0.025%.

TABLE 3

Effect of Polysorbate 80 on particle aggregation: Mechanical Agitation

| % (w/v) Polysorbate 80 | 0 rpm | 180 rpm | 240 rpm |
|---|---|---|---|
| 0.0% | 2200 | 140,000 | 570,000 |
| 0.0125% | 1800 | 110,000 | 710,000 |
| 0.025% | 2100 | 3700 | 18,000 |
| 0.05% | 1400 | 1100 | 5500 |

EXAMPLE 4

Determination of concentration of polysorbate 80 required to inhibit increases in filtration backpressure: mechanical agitation Hemoglobin was prepared as described in Example 2 and formulated in either 150 mM NaCl, 5 mM sodium phosphate, pH 7.4 (NaCl/sodium phosphate formulation) or 100 mM NaCl, 50 mM mannitol, 3 mM KCl, 2 mM $CaCl_2$, 1M $MgCl_2$ and 10 mM $NaHCO_3$, pH 7.6 (mannitol/bicarbonate formulation). Controls did not have polysorbate 80 added to the formulations while the test solutions of both the NaCl/sodium phosphate formulation and the mannitol/bicarbonate formulation contained 0.03% polysorbate 80. Aliquots (500 ml) of control and test hemoglobin solutions were placed in 1 L polycarbonate bottles and were agitated for 1 hour at 4° C. on an orbital shaker at 180 rpm. Following shaking, an aliquot (1 ml) of each sample was removed for particle content determination using the Hiac/Royco instrumentation as described above. The remaining volume of each sample was then transferred into a polyvinyl chloride bag and pumped through a 0.2 μm PALL in-line filter at 500 ml/hour using an IVAC infusion pump. The filter pressure was monitored directly from the IVAC pump.

The hemoglobin formulated without polysorbate 80 blocked the filter within 3 minutes irrespective of the other components of the solution (i.e. salts, etc.). In contrast, in the presence of polysorbate 80, ~500 ml of material formulated in either formulation did not cause overpressuring of the filter (backpressure greater than 500 mm Hg) during the course of the filtration. Filter blockage in the formulations that did not contain surfactant was most probably due to the approximately 300–400 fold increase in aggregates≧2 μm that resulted from mechanical agitation. After one hour of shaking, the mannitol/bicarbonate/no surfactant formulation contained>700,000 counts per ml, while the NaCl/sodium phosphate/no surfactant formulation contained>600,000 counts per ml. Counts per ml were determined using the Hiac/Royco Particle Counter described in Example 1.

EXAMPLE 5

Determination of concentration of polysorbate 80 required to inhibit increases in filtration backpressure: freeze/thaw Hemoglobin was prepared as described in Example 2 and formulated in either 150 mM NaCl, 5 mM sodium phosphate, pH 7.4 (NaCl/sodium phosphate formulation) or 100 mM NaCl, 50 mM mannitol, 3 mM KCl, 2 mM $CaCl_2$, 1 mM $MgCl_2$ and 10 mM $NaHCO_3$, pH 7.6 (mannitol/bicarbonate formulation). Controls did not have polysorbate 80 added to the formulations while the test solutions of both the NaCl/sodium phosphate formulation and the mannitol/bicarbonate formulation contained 0.03% polysorbate 80. Aliquots (500 ml) of control and test hemoglobin solutions were placed in 1 L polycarbonate bottles and frozen at −20° C. for 24 hours, then thawed in a 25° C. water bath. The freezing and thawing cycles were repeated three times. After the freeing and thawing, each sample was transferred into a polyvinyl chloride bag and pumped through a 0.2 μm PALL inline filter at 500 ml/hour using an IVAC infusion pump. The filter pressure was monitored directly from the IVAC pump.

Figure 1:
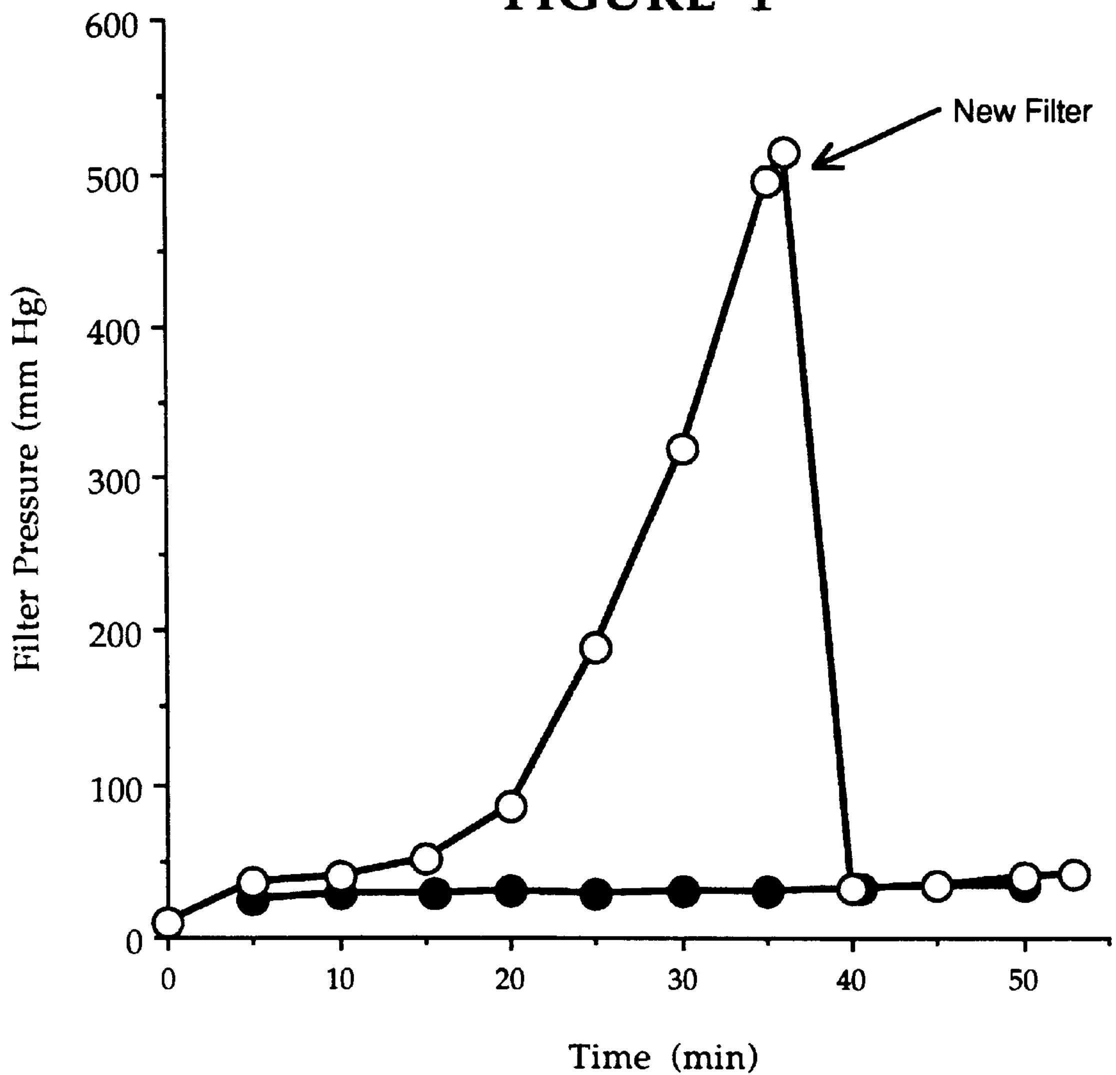
FIG. 1 shows filter pressure during filtration of hemoglobin formulated in a mannitol/bicarbonate buffer system.

Filtration of the material containing polysorbate 80 demonstrated no increase in filter pressure for both formulations (FIGS. 1 and 2). In contrast, the sample in the mannitol/bicarbonate formulation that did not contain polysorbate 80 achieved maximum filter pressure within 35 minutes. After replacement of the filter, backpressure again began to rise following another 12 minutes of filtration (FIG. 1). The NaCl/sodium phosphate/no polysorbate formulation exhibited behavior similar to the mannitol/bicarbonate formulation that did not contain surfactant. Filtration of the NaCl/sodium phosphate/no polysorbate formulation resulted in increasing filtration backpressure during the 50 minutes of filtration (FIG. 2).

EXAMPLE 6

Determination of Concentration of Polysorbate 80 required to inhibit formation of aggregates≧2 μm during mechanical agitation in the presence of EDTA Hemoglobin was prepared as described in Example 2. Suitable concentrations of polysorbate 80 for reduction of aggregation were determined by subjecting hemoglobin formulated with increasing concentrations of polysorbate 80 to mechanical agitation. Aliquots (1.5 ml) of 83 mg/ml hemoglobin in 150 mM NaCl, 5 mM phosphate, 25 μM EDTA, pH 7.4, were formulated with and without polysorbate 80 and were sealed in 3.5 ml glass vials. These samples were then shaken for 1.5 hours at 25° C. and 150 rpm on a rotary shaker. A 1 ml aliquot was removed and aggregates≧2 μm were counted using a HIAC/Royco Particle counter as described in Example 1. As in the case with no EDTA, addition of the surfactant at a concentration of ~0.03% or greater inhibited the formation of aggregates.

TABLE 4

Effect of Polysorbate 80 on particle aggregation in the presence of EDTA: Mechanical Agitation

| % (w/v) Polysorbate 80 | Time on shaker (hours) | Counts ≧2 μm |
|---|---|---|
| 0.0% | 0 | 4300 |
| 0.0% | 1.5 | 107,000 |
| 0.03% | 1.5 | 6400 |
| 0.045% | 1.5 | 4000 |
| 0.06% | 1.5 | 3800 |

The foregoing description of the invention is exemplary for purposes of illustration and explanation. It will be apparent to those skilled in the art that changes and modifications will be possible without departing from the spirit and the scope of the invention. It is intended that the following claims be interpreted to embrace all such changes and modifications.

We claim:

1. A composition comprising hemoglobin and a stabalizing amount of a surfactant, wherein the surfactant is not an adduct of a polymer and an anionic ligand.

2. The composition according to claim 1 wherein the surfactant is a non-ionic surfactant.

3. The composition according to claim 2 wherein the surfactant is selected from the group consisting of polyoxamer fatty acid esters and polyoxyethelene sorbitan fatty acid esters.

4. The composition according to claim 3 wherein the polyoxyethelene sorbitan fatty acid ester is polysorbate 80.

5. The composition according to claims 1, 2 or 3 wherein the surfactant is 0.02 to 0.5% by weight.

6. The composition according to claim 5 wherein the surfactant is 0.025 to 0.08% by weight.

7. The composition according to claim 1 further comprising:

about 0.001% to about 90% by weight to volume of hemoglobin

0–200 mM of at least one buffer;

0–200 mM of at least one alchohol or polyalchohol;

0–300 mM of at least one salt;

0.01–1% of at least one surfactant;

0–5 mM of at least one reducing agent;

0–100 μM of at least one chelating agent; and pH of about 6.5–9.5.

8. The composition according to claim 7 further comprising:

about 0.01% to about 50% by weight to volume of hemoglobin;

0–50 mM of at least one buffer;

0–200 mM of at least one salt;

0.02–0.5% of at least one surfactant;

0–5 mM of at least one reducing agent;

5–50 μM of at least one chelating agent; and pH of about 6.8–7.8.

9. The composition according to claim 8 further comprising:

about 1% to about 20% by weight to volume of hemoglobin;

5–20 mM of sodium phosphate;

100–175 mM of sodium chloride;

0.02–0.08% of polysorbate;

1–4 mM of ascorbate;

2–40 μM of ethylene diamine tetraacetic acid; and pH of about 6.8–7.6.

10. The composition according to claims 7 or 8 wherein the salts are chloride salts.

11. The composition according to claims 7 or 8 wherein the buffers are phosphate buffers.

12. The composition according to claims 7 or 8 wherein the surfactant is a polysorbate.

13. The composition according to claim 12 wherein the surfactant is polysorbate 80.

14. The composition according to claims 7 or 8 wherein the chelating agent is selected from the group consisting of ethylene diamine tetraacetic acid and ethylene glycol-bis(β-aminoethyl ether)N,N,N',N',-tetraacetic acid.

15. The composition of claim 14 wherein the chelating agent is ethylene diamine tetraacetic acid.

16. The composition according to claims 7 or 8 wherein the reducing agent is ascorbate.

17. A method of stabilizing a hemoglobin-containing composition comprising formulating the composition with a stabilizing amount of a surfactant, wherein the surfactant is not an adduct of a polymer and an anionic ligand.

18. The method according to claim 17 wherein the surfactant is a non-ionic surfactant.

19. The method according to claim 18 wherein the surfactant is selected from the group consisting of polyoxamer fatty acid esters and polyoxyethelene sorbitan fatty acid esters.

20. The method according to claim 19 wherein the polyoxyethelene sorbitan fatty acid ester is polysorbate 80.

21. The method according to claims 18, 19 or 20 wherein the surfactant is 0.02 to 0.5% by weight.

22. The method according to claim 21 wherein the surfactant is 0.025 to 0.08% by weight.

23. The method according to claim 17 wherein the composition comprises:

about 0.001% to about 90% by weight to volume of hemoglobin;

0–200 mM of at least one buffer;

0–200 mM of at least one alchohol or polyalchohol;

0–300 mM of at least one salt;

0.01–1% of at least one surfactant;

0–5 mM of at least one reducing agent;

0–100 μM of at least one chelating agent; and pH of about 6.5–9.5.

24. The method according to claim 23 wherein the composition comprises:

about 0.01% to about 50% by weight to volume of hemoglobin;

0–50 mM of at least one buffer;

0–200 mM of at least one salt;

0.02–0.5% of at least one surfactant;

0–5 mM of at least one reducing agent;

5–50 μM of at least one chelating agent; and pH of about 6.8–7.8.

25. The method according to claim 24 wherein the composition comprises:

about 1% to about 20% by weight to volume of hemoglobin;

5–20 mM of sodium phosphate;

100–175 mM of sodium chloride;

0.02–0.08% of polysorbate;

1–4 mM of ascorbate;

2–40 μM of ethylene diamine tetraacetic add; and pH of about 6.8–7.6.

26. The method of claims 23 or 24 wherein the salts are chloride salts.

27. The method of claims 23 or 24 wherein the buffers are phosphate buffers.

28. The method of claims 23 or 24 wherein the surfactant is a polysorbate.

29. The method according to claim 28 wherein the surfactant is polysorbate 80.

30. The method according to claims 23 or 24 wherein the chelating agent is selected from the group consisting of ethylene diamine tetraacetic add and ethylene glycol-bis(β-aminoethyl ether)N,N,N',N',-tetraacetic acid.

31. The method according to claim 30 wherein the chelating agent is ethylene diamine tetraacetic acid.

32. The method according to claims 23 or 24 wherein the reducing agent is ascorbate.

33. A method for the prevention of the formation of aggregates of hemoglobin molecules during storage comprising the addition of a stabilizing amount of surfactant to a solution containing hemoglobin prior to storage.

* * * * *

UNITED STATES PATENT AND TRADEMARK OFFICE
CERTIFICATE OF CORRECTION

PATENT NO : 5,914,391
DATED : June 22, 1999
INVENTOR(S) : Michael J. Gerber et al.

It is certified that error appears in the above-identified patent and that said Letters Patent is hereby corrected as shown below:

Column 12, claim 25, line 23, "add" should read ---acid---.

Column 12, claim 30, line 31, "add" should read ---acid---.

Signed and Sealed this

Eleventh Day of July, 2000

Attest:

Q. TODD DICKINSON

*Attesting Officer* *Director of Patents and Trademarks*